United States Patent [19]

Winters

[11] Patent Number: 4,612,318

[45] Date of Patent: Sep. 16, 1986

[54] CNS-DEPRESSANT AND ANALGESIC TRICYCLO-[PYRAZOLO-[3,4-6]-PYRIDINE] DERIVATIVES AND PHARMACEUTICAL COMPOSITIONS THEREOF

[75] Inventor: Giorgio Winters, Milan, Italy

[73] Assignee: Gruppo Lepetit S.p.A., Italy

[21] Appl. No.: 533,909

[22] Filed: Sep. 19, 1983

[30] Foreign Application Priority Data

Sep. 22, 1982 [IT] Italy ................ 22375 A/82

[51] Int. Cl.$^4$ .................. A61K 31/415; C07D 471/04
[52] U.S. Cl. ....................... 514/293; 546/82
[58] Field of Search .............. 546/64, 82, 85, 87, 546/119; 424/256; 514/293, 303

[56] References Cited

U.S. PATENT DOCUMENTS 3,403,158  9/1968  Markillie ...................... 546/119
3,903,096  9/1975  Denzel ......................... 546/119

OTHER PUBLICATIONS

Grandberg et al., CA, vol. 63, 1965, 63:5625g.
Troitskaya et al., CA, vol. 67, 1967, 67:116403w.
Higashino et al., Index Chemicus, vol. 66, 1977, 259367.

Primary Examiner—Henry R. Jiles
Assistant Examiner—J. G. Mullins
Attorney, Agent, or Firm—William J. Stein; Stephen L. Nesbitt

[57] ABSTRACT

The present invention refers to a new class of pyrazolopyridines having analgetic, anxiolytic, antiinflammatory and CNS-depressant activity. It is described a process for producing the compounds as well as pharmaceutical compositions containing them.

4 Claims, No Drawings

CNS-DEPRESSANT AND ANALGESIC TRICYCLO-[PYRAZOLO-[3,4-6]-PYRIDINE] DERIVATIVES AND PHARMACEUTICAL COMPOSITIONS THEREOF

The present invention relates to a new class of pyrazolo, pyridine derivatives having CNS-depressant, anxiolytic, analgetic, antiinflammatory activity, to a process for producing them and to pharmaceutical compositions containing them.

The new pyrazolo pyridines of the present invention are pyrazolo pyridine derivatives of the following formula I

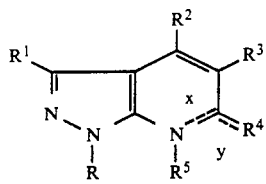

and their physiologically acceptable acid addition salts, wherein

R and $R^1$ independently represent $(C_{1-6})$alkyl, $(C_{3-7})$cycloalkyl, phenyl, substituted phenyl, phenyl$(C_{1-4})$alkyl, substituted phenyl$(C_{1-4})$alkyl;

$R^2$ represents hydrogen, $(C_{1-4})$alkyl, phenyl, substituted phenyl, phenyl$(C_{1-4})$alkyl, substituted phenyl$(C_{1-4})$alkyl;

$R^3$ represents $(C_{1-4})$alkyl, phenyl, substituted phenyl, phenyl$(C_{1-4})$alkyl, substituted phenyl $(C_{1-4})$alkyl, or $R^2$ and $R^3$ taken together represent a —$(CH_2)_n$— group wherein n is an integer selected from 3, 4, 5 and 6 and a —$CH_2$— group may be substituted with a

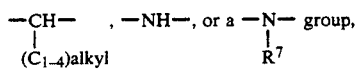

wherein $R^7$ represents $(C_{1-4})$alkyl or $(C_{2-6})$alkanoyl;

$R^4$ represents $R^8$, —$OR^9$ or an oxygen atom;

$R^8$ represents hydrogen, $(C_{1-4})$alkyl, phenyl, substituted phenyl, phenyl$(C_{1-4})$alkyl, substituted phenyl$(C_{1-4})$alkyl;

$R^9$ represents hydrogen, $(C_{1-4})$alkyl, $(C_{2-6})$alkanoyl-$(C_{1-4})$alkyl, hydroxy$(C_{2-4})$alkyl, halo$(C_{2-4})$alkyl, amino$(C_{2-4})$alkyl, mono- or di-$(C_{1-4})$alkylamino$(C_{2-4})$alkyl, or disubstituted amino$(C_{2-4})$alkyl, wherein the nitrogen atom is part of a 4, 5, 6 or 7 membered saturated heterocyclic ring which may contain a further heteroatom selected from N, S, and O and may optionally be substituted with a substituent selected from $(C_{1-4})$alkyl, $(C_{5-7})$cycloalkyl, phenyl, substituted phenyl, phenyl$(C_{1-4})$alkyl and substituted phenyl$(C_{1-4})$alkyl;

$R^5$ represents $R^9$ as above defined when $R^4$ is oxygen, y is an additional bond and x is nil, or $R^5$ represents nil when x is an additional bond, y is nil and $R^4$ represents $R^8$ or $OR^9$; with the proviso that when R, $R^1$ and $R^2$ are defined as above, $R^4$ is oxygen, y is an additional bond, both x and $R^9$ are nil, $R^3$ must be different from $(C_{1-4})$alkyl and with the further proviso that when R, $R^1$, and $R^3$ are defined as above, $R^4$ is $R^8$, y is nil, and x is an additional bond, $R^2$ must be different from methyl.

As used herein, the term $(C_{1-6})$alkyl alone or in combination with other groups, represents a straight or branched alkyl group of from 1 to 6 carbon atoms such as methyl, ethyl, n-propyl, iso-propyl, n-butyl, tert-butyl, n-pentyl, n-hexyl and the like.

The term "$(C_{1-4})$alkyl" alone or in combination with other groups represents a straight or branched alkyl group of from 1 to 4 carbon atoms.

The term "$(C_{1-4})$alkoxy", alone or in combination, represents straight or branched alkoxy groups such as methoxy, ethoxy, propoxy, butoxy and the like.

The term "$(C_{3-7})$cycloalkyl" represents cycloalkyl rings of from 3 to 7 carbon atoms, such as cyclopropyl, cyclobutyl, cyclopentyl, cyclohexyl, and cycloheptyl.

The term "$(C_{2-6})$alkanoyl", represents alkanoyl groups of from 2 to 6 carbon atoms such as acetyl, propionyl, butirryl, n-valeryl, trimethylacetyl, caproyl, and the like.

The term "hydroxy$(C_{2-4})$alkyl", identifies straight or branched hydroxyalkyl radicals such as 2-hydroxyethyl, 3-hydroxypropyl, 2-hydroxypropyl, 4-hydroxybutyl, 2-hydroxybutyl or 2-hydroxy-2-methylpropyl.

The term "halo$(C_{2-4})$alkyl", identifies straight or branched haloalkyl radicals such as 2-chloroethyl, 2-bromoethyl, 3-chloropropyl, 2-chloropropyl, 3-bromopropyl, 2-bromopropyl, 4-bromobutyl, 4-chlorobutyl, 3-bromobutyl, 3-chlorobutyl, 2-bromobutyl, 2-chlorobutyl, 2-bromo-2-methylpropyl, 2-chloro-2-methylpropyl, 2-iodoethyl, 3-iodopropyl, or 4-iodobutyl.

The term "substituted phenyl" alone or in combination with other groups, refers to a phenyl group wherein one, two or three hydrogen atoms are replaced by substituents independently selected from, chloro, bromo, fluoro, cyano, nitro, hydroxy, mercapto, trifluoromethyl, $(C_{1-4})$alkyl, $(C_{2-4})$alkenyl, $(C_{2-4})$alkynyl, $(C_{3-7})$cycloalkyl, $(C_{1-4})$alkoxy, $(C_{1-4})$alkylthio, $(C_{1-4})$alkoxycarbonyl, carboxy$(C_{1-4})$alkyl, carboxy$(C_{3-7})$cycloalkyl, sulfynyl, $(C_{1-4})$alkylsulfynyl.

The term "4, 5, 6 or 7 membered saturated heterocyclic ring" refers to saturated heterocyclic groups of from 4 to 7 atoms such as: azetidinyl, pyrrolidyl, piperidinyl, 4-aminopiperidinyl, 4-alkylamino-piperidinyl, piperazinyl, morpholinyl, thiomorpholinyl, 4-methylpiperazinyl, 4-phenylpiperazinyl, 2,6-dimethylpiperazinyl, 3,3-dimethylpiperazinyl, 2,6-dimethylmorpholynyl, and the like.

The term "halo" represents chlorine, bromine or iodine atoms.

"Inert organic solvent", as used in the description of the present invention, is a solvent in which the reactants are sufficiently soluble to allow the reaction to proceed, but which does not unfavourably interfere with the reactants or the final products. "Physiologically acceptable salts" are pharmaceutically acceptable salts wherein the whole toxicity of the compound is not increased compared with the non-salt. From these, acid addition salts are obtained by treating compounds of formula I above with pharmaceutically acceptable acids. As acids suitable for the formation of therapeutically acceptable salts there may be mentioned, for example, hydrohalide, sulfuric, phosphoric, and nitric acids; aliphatic, alicyclic, aromatic or heterocyclic carboxylic or sulfonic acids, such as formic, acetic, propionic, succinic, glycolic, lactic, malic, tartaric, citric, ascorbic, α-chetoglutaric, glutammic, aspartic, maleic, hydroxymaleic, pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid. These or other salts of the new compounds may also be used for purifying the resulting compounds by converting them into salts, isolating the latter and liberating the free bases from them. When according to the above outlined processes, compounds of formula I are obtained as the corresponding salts of pharmaceutically acceptable acids, they may be converted into the corresponding free base compounds with a suitable alkali agent. The free bases may in turn be transformed into the corresponding salts by reaction with predetermined pharmaceutically acceptable acids. In view of the close relationship between the new compounds in the free form and in the form of their salts what has been said above and hereinafter with reference to the free compounds concerns also the corresponding salts.

A preferred group of compounds of the invention includes those compounds of formula I wherein R represents $(C_{1-6})$alkyl, $R^1$ is a methyl group, $R^2$ and $R^3$ taken together represent $—(CH_2)_n—$, wherein n is an integer selected from 3, 4, 5, 6 or a $—CH_2—$ group may be substituted with a

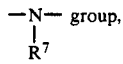

wherein $R^7$ is $(C_{1-4})$alkyl or alkanoyl. $R^4$ represents $OR^9$ wherein $R^9$ is selected from $(C_{1-4})$alkyl and hydroxy$(C_{1-4})$alkyl, $R^5$ is nil, x is an additional bond and y is nil.

Another preferred group of compounds of the invention includes those compounds of formula I wherein R represents $(C_{1-6})$alkyl, $R^4$ represents an oxygen atom, $R^5$ represents mono- or di-$(C_{1-4})$alkylamino$(C_{1-4})$alkyl or disubstituted amino$(C_{1-4})$alkyl, wherein the nitrogen atom is part of a 5 or 6 membered saturated heterocyclic ring which may contain a further heteroatom selected from O and N and may be substituted with one $(C_{1-4})$alkyl or phenyl group.

Another preferred group of compounds of the invention includes those compounds of formula I wherein R is $(C_{1-6})$alkyl or $(C_{3-7})$cycloalkyl, $R^1$ represents $(C_{1-4})$alkyl, $R^2$ and $R^3$ independently represent $(C_{1-4})$alkyl or phenyl, or $R^2$ and $R^3$ taken together represent $—(CH_2)—$ group wherein n is an integer selected from 3, 4, and wherein one of the $—(CH_2)—$ groups is substituted with a

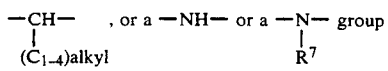

wherein $R^7$ is $(C_{1-4})$alkyl, $(C_{2-4})$alkanoyl group, $R^4$ represents $R^8$ as above defined, $R^5$ is nil, x is an additional bond and y is nil.

Isoquinoline derivatives, wherein the nitrogen atom bears a hydrogen atom are described in U.S. Pat. No. 4,113,713, while thiazolo and pyrazolo isoquinoline derivatives wherein the 4-nitrogen atom or the 5-oxygen atom are variously substituted are described in Europen Patent Publication No. 5745.

The compounds of the invention wherein R, $R^1$, $R^2$, $R^3$ are as defined above, $R^4$ represents $OR^9$, $R^5$ represents nil, x is an additional bond and y is nil, and the compounds of the invention wherein R, $R^1$, $R^2$, $R^3$ are as above $R^4$ is an oxygen atom and $R^5$ represents $R^9$, as above defined, x is nil and y is an additional bond, are prepared by a multistep procedure starting from a derivative of formula III according to Scheme I

SCHEME I

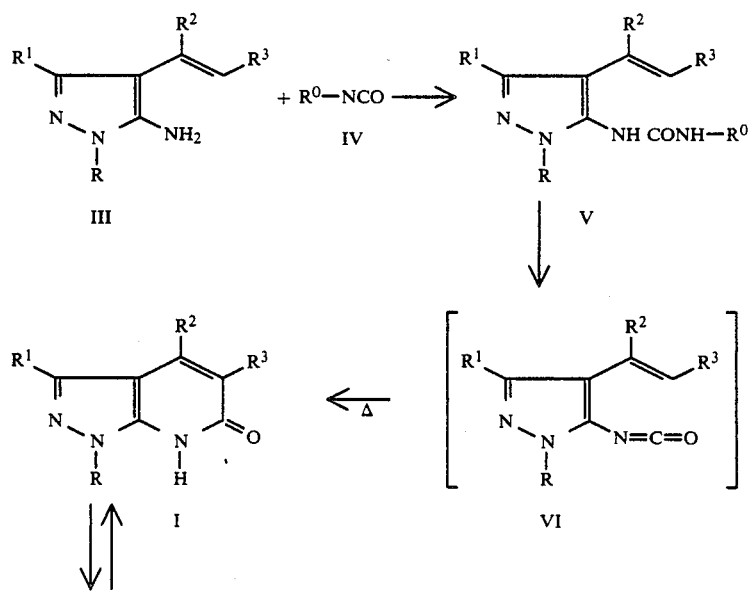

SCHEME I

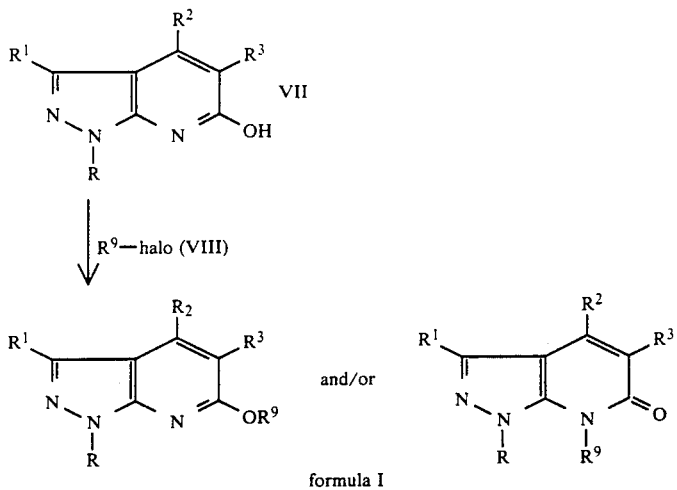

formula I

A compound of formula III, wherein the substituent groups are as above defined, is reacted with a isocyanate derivative of formula IV (R°—N=C=O), in a suitable solvent, in equimolecular amounts or in the presence of an excess of the compound IV, at a temperature between −5° C. and 50° C., preferably between room temperature and the reflux temperature. The reaction time generally varies from a few minutes to some hours, depending on the compounds involved and the reaction temperature. This reaction step is carried out in the presence of a base.

Representative examples of suitable base are aromatic or aliphatic tertiary amines such as 4-picoline, pyridine, triethylamine, trimethylamine and the like. According to a preferred embodiment of the invention, these basic agents can be used also as the reaction solvent. In this reaction, one may employ one of a large number of isocyanate derivatives, since the essential feature of the R° group is a good leaving group capability without interfering with the reaction course.

Examples of such leaving groups are lower alkyl or aryl groups such as ethyl, propyl, isopropyl, butyl, phenyl, p-tolyl and the like.

Suitable solvents are inert organic solvents such as benzene, toluene, xylene, ethyl acetate, ($C_{3-10}$)ethers, dioxane, ($C_{5-7}$)cycloalkanes and the like.

According to this procedure, an intermediate compound of formula V is obtained and, after recovering it according to common procedures, or directly, without recovery, the substance or reaction mixture is dispersed in a suitable organic solvent or solvent mixture and heated at a temperature between 50° C. and the reflux temperature, preferably from about 90° C. to about 250° C. The reaction time generally is from 1 minute to 8 hours, depending on the other reaction conditions. A reaction product is recovered, which is the compound of formula VII. This compound of formula VII (i.e. a compound of formula I wherein R, $R^1$, $R^2$, $R^3$ are as above defined, $R^4$ represents $R^9$ when $R^9$ is hydrogen, $R^5$ is oxygen, x is nil and y is an additional bond), is then reacted with an equimolecular amount or a discrete excess of a halide of formula VIII $R^9$—halo, wherein $R^9$ is defined as above with the exception of hydrogen and halo is an halogen atom selected from chlorine, bromine and iodine and preferably bromine or iodine to give the compounds of formula I.

When $R^9$ is a ($C_{1-4}$)alkyl group, also ($C_{1-4}$)alkylsulfonates may be advantageously employed instead of the halide VIII.

The process is carried out by dissolving or suspending a molar amount of the selected compound of formula V in an inert organic solvent, such as, for instance, dioxane, tetrahydrofuran or, preferably, dimethylformamide, and adding to the obtained solution or suspension an equimolecular amount or a slight excess of a strong alkali agent over the compound of formula VII.

Suitable alkali agents may be selected from alkali alkoxides such as, for instance, sodium methoxide, sodium ethoxide or potassium tert-butoxide, alkali metals and, preferably, alkali hydrides, e.g. sodium or potassium hydride. The obtained reaction mixture is kept for 2–3 hours at a temperature between 50° and 70° C., preferably at about 60° C., then, after cooling to room temperature, a slight molar excess of the compound of formula VIII is added and the mixture is heated for about 1–2 hours at a temperature again between about 50° and about 70° C., preferably at about 60° C.

The mixture is finally worked up according to conventional techniques. Pursuant to this procedure, mixtures of the end compounds of formula I, wherein the substituent $R^9$ is linked either to the nitrogen atom or to the oxygen atom, may be obtained in different percentages. The percentage of each isomer essentially depends on the nature of the substituents, although a general rule cannot be established. In general, it has been found that, with the molecules described in the present application, the O-substituted compounds are mainly obtained.

In any case, when a mixture of N-substituted and O-substituted compounds is obtained, the single isomers can be isolated by means of common separation techniques, such as column chromatography, fractioned crystallization, HPLC and the like.

Some of the compounds of the invention can advantageously be prepared by other routes which involve the transformation of a preexisting $R^9$ substituent into another one falling within the scope of the invention. As an example, the compounds of formula I wherein $R^9$ is halo($C_{2-4}$)alkyl, are useful starting materials for preparing the corresponding compounds of formula I wherein $R^9$ represents an aminoalkyl or substituted amino($C_2$-

4)alkyl as above defined. These compounds are prepared simply by reacting the selected halo($C_{2-4}$)alkyl derivative with the suitable amine derivative according to known procedure.

It has been found that compounds of formula I wherein $R^9$ is halo($C_{2-4}$)alkyl may be conveniently prepared from the corresponding hydroxy($C_{2-4}$)alkyl derivatives by reacting it with appropriate halogenating agents, such as thionyl or phosphoryl halides and phosphorus pentahalides.

It has been observed, however, that, when this halogenation reaction is carried out on a substrate of

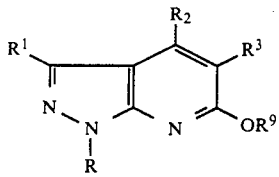

wherein R, $R^1$, $R^2$ and $R^3$ have the same meanings as before and $R^9$ is a 2-hydroxyethyl or a 3-hydroxypropyl group, the reaction does not always afford the corresponding halo derivative in considerable yields, but a rearrangement may occur and the N-isomer of the following formula

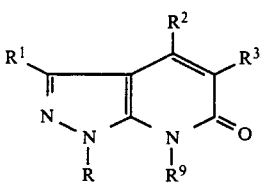

wherein R, $R^1$, $R^2$, $R^3$ are defined as above and $R^9$ represents a 2-haloethyl or a 3-halopropyl group, in which halo stands for a halogen atom, may be obtained in good yields. The reaction is advantageously performed by dissolving or suspending a suitable amount of the compound of formula VII in an organic solvent such as, for instance, a ($C_{1-4}$)halogenated hydrocarbon and adding to the obtained solution or suspension a molar excess of the halogenating agent, preferably from about 1 to about 3 molar equivalents over the starting compound of formula VII. Although all of the common halogenating agents proved to act satisfactorily, it has been found that the best results are obtained by employing thionyl halides, e.g. thionyl chloride or thionyl bromide. The reaction is carried out at a temperature between room temperature and about 70° C., and is complete in about 1-4 hours.

In turn, the compounds of formula I wherein $R^9$ represents halo($C_{2-4}$)alkyl can be transformed into the corresponding derivatives of formula I wherein $R^4$ represents an oxygen atom and $R^9$ represents amino($C_{2-4}$)alkyl, mono- or di-substituted amino($C_{2-4}$)alkyl or disubstituted amino($C_{2-4}$)alkyl wherein the nitrogen atom is part of a 4, 5, 6 or 7 membered saturated heterocyclic ring, by reacting it with the proper amine according to usual procedures.

Finally, it will be clear to any person skilled in the art that other obvious routes for transforming a preexisting radical $R^9$ into another radical $R^9$ emcompassed by the present invention are intended to fall within the scopes of the invention.

The compounds of formula I wherein R, $R^1$, $R^2$ and $R^3$ are as above defined, $R^4$ represents $R^8$, $R^5$ is nil, x is an additional bond and y is nil are prepared according to the following scheme II

SCHEME II

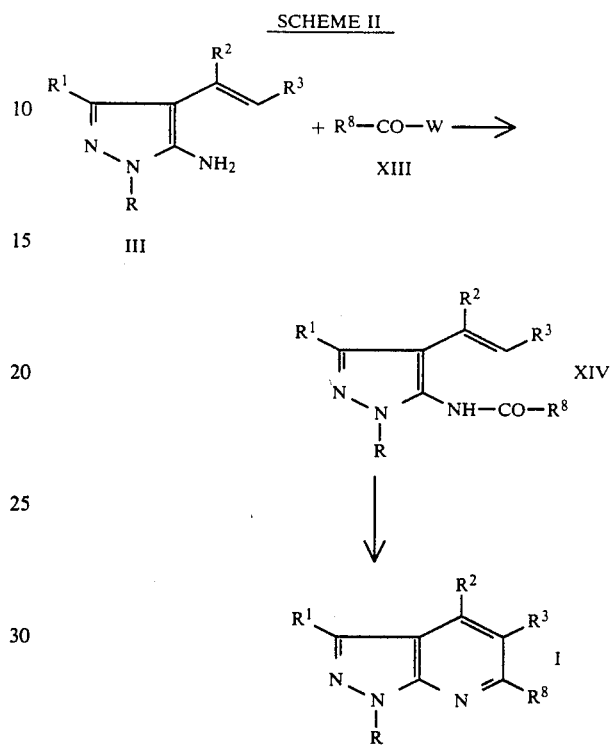

According to this procedure, a compound of formula III is reacted with an equimolecular amount or a slight excess of a carboxylic acid derivative (such as a carboxylic acid halide, ester or anhydride) of the following formula XIII $R^8$—CO—W          XIII wherein $R^8$ is as above and W represents an halogen atom selected from chlorine, bromine, and iodine, a O—R°° or a —O—CO—$R^8$ group, wherein R°° represents, together with the adjacent O atom, a "good leaving group" which does not interfere with the reaction course. The skilled man is aware of the large number of such compounds, examples of which include lower alkyl, cycloalkyl or aryl groups such as methyl, ethyl, propyl, isopropyl, butyl, cyclohexyl, phenyl, tolyl, and the like.

The reaction solvent is an anhydrous inert organic solvent such as those previously disclosed and includes: ($C_{3-10}$)ethers, chloro($C_{1-3}$)alkanes, xylene, toluene, benzene, carboxylic acid such as formic acid and the like, and carboxylic acid anhydrides such as acetic acid anhydride and the like.

In some instances, the carboxylic acid anhydride can be properly selected so that it can act as the reactant as well as the reaction solvent.

The reaction temperature is between room temperature and the reflux temperature and preferably is the reflux temperature. The reaction time is generally between 2 and 6 hours or more. The recovery of the compound of formula XIV so obtained is achieved through common procedures.

The compound of formula XIV is then reacted with a substance capable of helping the cyclization by acting as a catalyst such as, for example, thionyl and phosphoryl halides in an inert organic solvent, such as a petroleum distillate boiling between 100° C. and 250° C., xylene, toluene, benzene, cyclohexane, cyclopentane, methylene chloride and the like at a temperature varying from room temperature to the reflux temperature of the mixture. The reaction time is from few minutes to about 25 hours. The reaction product is then recovered through common procedures. Generally, the solvent is distilled off under vacuum. The residue is taken up with water and the pH is adjusted to about 8.

After extraction with a suitable organic solvent, such as methylene chloride, and distillation of the solvent under reduced pressure, the desired product of formula I wherein R, $R^1$, $R^2$ and $R^3$ are as above defined, $R^4$ represents $R^8$, $R^5$ is nil, x is an additional bond and y is nil, is obtained.

The pyrazolamines of formula III are prepared reacting a pyrazolamine derivative of formula

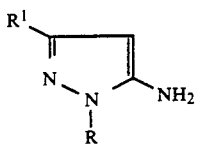

with an equimolecular amount or an excess of a carbonyl compound of formula

$$R^2COCH_2R^3$$

wherein $R^2$ and $R^3$ are as defined.

The reaction solvent is preferably an organic acid solvent, and most preferably is a lower organic acid solvent such as propionic or acetic acid. The temperature of the mixture is kept between room temperature and the reflux temperature.

The reaction time obviously depends on the different reagents and the reaction temperature, but generally is between a few hours to some days, frequently between 2 hours and 3 days.

As stated above, the compounds of the invention possess interesting analgetic, CNS-depressant, antianxiety, and antiinflammatory activity. These activities are generally shared also by some intermediates.

The compounds of the invention, generally have a considerably low toxicity, since most of their $LD_{50}$ values are higher than 500 mg/kg, when given intraperitoneally and rarely lower than 950 mg/kg when given orally to mice.

The analgesic activity of the compounds of the present invention was ascertained by means of two known tests for analgesia: the "writhing test" in mice, described by L.C. Hendershot and J. Forsaith, in J. Pharm. Exp. Therap. 125, 237, (1959), and the "pain relief test" in rats described by L. O. Randall and J. J. Selitto, in Arch. Int. Pharmacodyn. 111, 409, (1957). In the former the disappearance or the reduction of writhing in mice, intraperitoneally administered, with p-phenylquinone—a substance known to produce pain especially in the place of injection—is evaluated; the latter test is used to evaluate the ratio of relief from the pain due to compression of oedema paws in rats orally administered with the test compound.

A compound which proved to be highly effective in these tests is that of example 57; a good activity is also shown for instance by the compounds of examples 39 and 55.

The above compounds of the invention are from 2 to 10 times as active acetylsalicylic acid in these tests.

The following tables summarize the data obtained assaying the compound of example 57 (co. 57) in comparison with acetylsalicylic acid (ASA) in the above tests:

| (a) "writhing test" | | |
|---|---|---|
| | dosage (mg/kg) per os | percent of inhibition of writhings |
| co. 57 | 10 | 25 |
| | 20 | 51 |
| | 50 | 89 |
| ASA | 20 | 10 |
| | 50 | 57 |
| | 100 | 86 |
| potency ratio co. 57:ASA = 6.6 | | |

| (b) "pain relief test" | | |
|---|---|---|
| | dosage (mg/kg) per os | percent of increase of the pain threshold |
| co. 57 | 20 | 78 |
| | 50 | 115 |
| | 100 | 172 |
| ASA | 50 | 39 |
| | 100 | 84 |
| | 300 | 109 |
| potency ratio co. 57:ASA = 2.6 | | |

The $LD_{50}$ values of co. 57 in orally administered rats is 650 mg/kg, while its $LD_{50}$ value in orally administered mice is higher than 1000 mg/kg.

The antiinflammatory activity was ascertained by means of the "carrageenin-induced oedema test" in rats. Said test is performed essentially following the procedure proposed by C. A. Winter et al. in Proc. Soc. Exptl. Biol. Med. 111, 544, (1962). It was found that oral dosages of between about 1/25 and 1/5 of the $LD_{50}$ values of the compounds of examples 4, 5, and 48 cause a significant reduction of the oedema over the controls, from about 30% to about 65% depending also on the actual dose.

The CNS-depressant activity was investigated by means of the general psychophysic screening method, as described by S. Irwin in Psychopharmacologia (Berl.) 13, 222–257, (1968). In particular, some representative experiments carried out in mice have shown that amounts from about 5 to about 100 mg/kg i.p. of the compounds of examples 32, 64 and 62 are effective in inhibiting the spontaneous activity and the muscular tone, whereas amounts from about 30 to about 200 mg/kg i.p. significantly impaired the motor coordination and the righting reflex of the laboratory animals. It is generally accepted that the above parameters are directly connected with sedative hypnotic and myorelaxant properties.

The anti-anxiety activity of the compounds of the invention was investigated by means of the "pole climbing avoidance test", performed essentially as described by G. Maffii, in Journ. Pharm. Pharmacol., 11 129, (1959). A conditioned animal, generally rat, is deconditioned, i.e. is brought to its normal psychic behaviour, by administration of a suitable amount of the compound to be tested. According to the authors, an inhibition of the secondary conditioned response ($CR_2$) without a contemporary or coupled with a not significant inhibition of the primary conditioned response (CR) and the unconditioned response (UR) is a clear indication of an anti-anxiety effect since these last two parameters are connected with sedative and hypnotic properties. Representative experiments carried out on groups of ten rats have shown that dosages varying from about 3 to about 60 mg/kg of body weight administered i.p. of the compounds of examples 1, 8, 18, 27, 28, 40, 44 and 45 are effective in inhibiting the $CR_2$-parameter and, contemporaneously, have no practical influence on the CR and the UR.

The compounds of the invention may be administered by different routes. While the preferred routes of administration are oral and rectal, parenteral administration can also be employed.

For oral administration, the compounds are compounded into pharmaceutical dosage forms, such as, for instance, tablets, capsules, elixirs, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives.

The dosage range is from about 0.05 to about 2.0 g per day, preferably administered in divided doses. Accordingly, the present invention provides a therapeutic composition comprising a compound of the invention as the active ingredient together with a pharmaceutically acceptable carrier.

The following examples illustrate the manner in which the invention can be practiced, but, as such, should not be construed as limiting its overall scope.

EXAMPLE 1

4-(1,2,5,6-tetrahydro-1-methyl-4-pyridinyl)-1,3-dimethyl 5-(1H)-pyrazolamine

1-Methyl-4-pyridinone (1.1 mole) is added to 1,3-dimethyl-5-pyrazolamine (1 mole). The reaction mixture is kept at a temperature between 70° C. and 80° C. for a period of about 8 hours. After distillation under vacuum the residue is poured into water and neutralized with NaOH 10%. The compound of the title is recovered by filtration. M.p. 262°–265° C.

Essentially following the above procedure, employing the carbonyl compound, molar rate, temperature and time as indicated in the following table I, the compounds of formula III

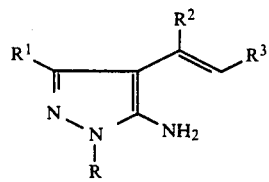

wherein R and $R^1$ are methyl groups and $R^2$ and $R^3$ are as shown below, are obtained.

TABLE I

| Example No. | Carbonyl compound | Molar ratio | Reaction temperature °C. | Reaction time (hours) | $R^2$ | $R^3$ | M.P. °C. |
|---|---|---|---|---|---|---|---|
| 2 | cyclopentanone | 2,2 | 60 | 8 | —(CH$_2$)$_3$— | | 130–131° |
| 3 | cyclohexanone | 2,0 | 25 | 45 | —(CH$_2$)$_4$— | | 176–179° |
| 4 | 4-methylcyclohexanone | 1,5 | 25 | 50 | —CH$_2$—CH$_2$—CH(CH$_3$)—CH$_2$— | | 140–142° |
| 5 | 3-methylcyclohexanone | 1,5 | 25 | 38 | —CH$_2$—CH(CH$_3$)—CH$_2$—CH$_2$— | | 152–153° |
| 6 | cycloheptanone | 3,0 | 75 | 30 | —(CH$_2$)$_5$— | | 138–139° |

TABLE I-continued

| Example No. | Carbonyl compound | Molar ratio | Reaction temperature °C. | Reaction time (hours) | R² | R³ | M.P. °C. |
|---|---|---|---|---|---|---|---|
| 7 | 1-acetyl-4-piperidone (structure: piperidone with N-COCH₃) | 1,1 | 75 | 15 | | —CH₂CH₂N(COCH₃)—CH₂— | 176–178° |
| 8 | 1-ethoxycarbonyl-4-piperidone (structure: piperidone with N-COC₂H₅) | 1,1 | 25 | 45 | | —CH₂CH₂—N(COC₂H₅)—CH₂— | 207–210° |
| 9 | CH₃COCH₂CH₂CH₃ | 4 | 50 | 8 | CH₃ | C₂H₅ | crude |
| 10 | CH₃COCH₂Cl | 1 | 60 | 8 | CH₃ | Cl | crude |
| 11 | C₆H₅—COCH₂CH₃ | 3 | 70 | 54 | C₆H₅ | CH₃ | 105–125° |
| 12 | C₆H₅—CH₂CHO | 1 | 25 | 58 | H | C₆H₅ | crude |

EXAMPLE 13

3-Phenyl-1-methyl-4-cyclohexyl-5-pyrazolamine

It is obtained by following essentially the procedure of example 1, reacting 1-phenyl-3-methyl-5-pyrazolamine with cyclohexanone (1:2, molar ratio) at a temperature of about 45° C. for about 8 hours. M.p. 212°–214° C.

EXAMPLE 14

1,3-Diphenyl-4-cyclohexenyl-5-pyrazolamine

It is obtained by essentially following the procedure of example 1, reacting 1,3-diphenyl-5-pyrazolamine (1 mole) with cyclohexanone (1.1 mole) at a temperature of about 80° C. for about 4 hours. M.p. 115°–117° C.

EXAMPLE 15

N-[4-(1-cyclopenten-1-yl)-1,3-dimethyl-1H-pyrazol-5-yl]-N'-phenylurea

Phenylisocyanate (0.176 mol) is added to 4-(1-cyclopenten-1-yl)-1,3-dimethyl-1H-pyrazol-5-amine (0.16 mol) in benzene (800 ml). The reaction mixture is stirred at room temperature and then at a temperature between 50° and 70° C. After distillation under vacuum, the product of the title is recovered by usual procedures. M.p. 204° C.

By following essentially the same procedure the compounds of examples 16 and 17 are obtained.

EXAMPLE 16

N-[4-(1-cyclohexen-1-yl)-1,3-dimethyl-1H-pyrazol-5-yl]-N'-phenylurea, m.p. 203° C., obtained starting from 4-(1-cyclohexen-1-yl)-1,3-dimethyl-1H-pyrazolamine and phenyl isocyanate.

EXAMPLE 17

N-phenyl-N'-[4-(1-phenyl-1-propenyl)-1,3-dimethyl-1H-pyrazol-5-yl]urea, m.p. 173°–195° C., obtained starting from 4-(1-phenyl-1-propenyl)-1,3-dimethyl-1H-pyrazol-5-amine with phenylisocyanate.

EXAMPLE 18

6,7,8,9-Tetrahydro-1,3-dimethyl-3H-pyrazolo[3,4-c]isoquinoline-5(4H)-one

N-[4-(1-cyclohexen-1-yl)-1,3-dimethyl-1H-pyrazol-5-yl]-N'-phenylurea (8.3 g) is fused at about 280° C., for 10 minutes. During the fusion, aniline distills off. The fused mass is cooled, triturated with methanol and heated to the reflux temperature. Upon cooling and filtering a solid is obtained which is washed with ethyl ether. Upon analysis it is proven to be the compound of the title. M.p. >300° C.

Essentially following the above procedure, the compounds of the examples 19 and 20 are obtained, by starting from the corresponding ureas, and carrying out the fusion respectively at about 200° C. and about 230° C. for 5 minutes.

EXAMPLE 19

3,6,7,8-Tetrahydro-1,3-dimethylcyclopenta[d]pyrazolo[3,4-b]pyridin-5-one

M.p. >300° C.

EXAMPLE 20

6,7,8,9-Tetrahydro-1,3-dimethyl-3H-pyrazolo[3,4-e]naphthiridin-5-(1H)-one, hydrochloride M.p. 228°–229° C.

EXAMPLE 21

3,6,7,8,9,10-Hexahydro-1,3-dimethylcycloheptan[d-]pyrazolo[3,4-b]pyridin-5-(4H)-one A mixture of the compound of example 6 (18.3 g), 4-picoline (100 ml) and ethylisocyanate (18 g) are heated to the reflux temperature for about 7 hours. After cooling to room temperature the solvent is distilled off under reduced pressure and the residue is taken up with ethyl ether and filtered. The recovered solid is boiled in methanol for 5 minutes. Upon filtering, the solid product of the title is recovered. An additional crop of the product may be obtained from the mother liquors. M.p. 269°–270° C.

EXAMPLE 22

6,7,8,9-Tetrahydro-1,3,7-trimethyl-3H-pyrazolo[3,4-c][2,7]naphthiridin-5-(4H)-one A mixture of the compound of example 7 (1 g; 0.0043 mol), 4-picoline (10 ml) and ethylisocyanate (1.22 g; 0.0172 mol) is heated to reflux temperature for about 3 hours. After cooling to room temperature, the solvent is distilled off under reduced pressure and the residue is taken up with ethyl acetate, then with ethyl ether and filtered giving the solid product of the title. M.p. >300° C. Another crop of this product can be obtained from the mother liquors.

EXAMPLE 23

5-Methoxy-3,6,7,8-tetrahydro-1,3-dimethylcyclopenta[d]pyrazolo[3,4-b]-pyridine

A mixture of 4-(1,2,5,6-tetrahydro-1-methyl-4-pyridinyl)-1,3-dimethyl-5-(1H)-pyrazolamine (2.06 g; 0.01 mol), 3,4-lutidine (20 ml), ethyl isocyanate (3.16 ml; 0.04 mol), under anhydrous conditions, are heated to the reflux temperature for about 3 hours. The mixture is then cooled to room temperature, concentrated under reduced pressure, washed with ethyl acetate and then with ethyl ether, thus obtaining the product of the title. M.p. 294°–297° C.

EXAMPLE 24

3,6,7,8-Tetrahydro-1,3,4-trimethylcyclopenta[d-]pyrazolo[3,4-b]-pyridin-5-(4H)-one (N-isomer) and 5-methoxy-3,6,7,8-tetrahydro-1,3-dimethyl-cyclopenta[d]pyrazolo[3,4-b]pyridine (O-isomer)

1.45 g of a 50% (by weight) suspension of sodium hydride in mineral oil (0.030 mole of sodium hydride) is added to a suspension of 3,6,7,8-tetrahydro-1,3-dimethyl-cyclopenta[d]pyrazolo[3,4-b]pyridin-5-(4H)-one (0.030 mol) in 64 ml DMF. The resulting mixture is kept at 60° C. for about 2 hours and, after cooling to room temperature, 2.37 ml (0.038 mole) of methyl iodide are added thereto. The mixture is then heated for 1 hour at about 60° C. After evaporating the solvent the residue is taken up with water and the obtained solid is collected by filtration, washed with water, taken up with DMF and applied to a silica gel chromatography column eluting with a mixture chloroform:methanol, 99:1. After recovery 45% of the O-isomer, m.p. 308°–310° C., and 25% of the N-isomer, m.p. 190°–191° C., are obtained.

Essentially following the procedure of the above example and employing the reagents, solvents and conditions indicated in table II below, compounds of the following formula

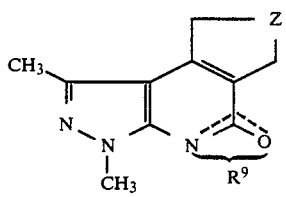

are obtained starting from the suitable derivatives of formula VII wherein $R^9$ is hydrogen.

TABLE II

| Example No. | Reagent | Basic compound | Solvent | Z | $R^9$ | Product | M.p. (b.p.) |
|---|---|---|---|---|---|---|---|
| 25 | HOCH$_2$CH$_2$Br | NaH | DMF[(1)] | —CH$_2$— | CH$_2$CH$_2$OH | O—isomer | 148–158° |
| 26 | CH$_3$I | NaH | DMF | —(CH$_2$)$_2$— | CH$_3$ | O—isomer | 90–95° |
|  | CH$_3$J | NaH | DMF | —(CH$_2$)$_2$— | CH$_3$ | N—isomer | 125–127° |
| 27 | n-C$_4$H$_9$Br | NaH | DMF | —(CH$_2$)$_2$— | nC$_4$H$_9$ | O—isomer | 145°/0.4 mmHg |
| 28 | HO—CH$_2$CH$_2$Br | NaH | DMF | —(CH$_2$)$_2$— | CH$_2$CH$_2$OH | O—isomer | 103–106° |
| 29 | CH$_3$I | NaH | DMF | —CH$_2$—N—<br>         COCH$_3$ | CH$_3$ | O—isomer | 196–172° |
|  | CH$_3$J | NaH mx,1 K$_2$CO$_3$ | DMF DME[(2)] | —CH$_2$—N—<br>         COCH$_3$ | CH$_3$ | N—isomer | 169–172° |
| 30 | HO—CH$_2$CH$_2$Br | K$_2$CO$_3$ | DMF | —CH$_2$—N—<br>         COCH$_3$ | CH$_2$CH$_2$OH | O—isomer | 169–171° |
| 31 | HO—CH$_2$CH$_2$Br | NaH | DMF | —CH$_2$—N—<br>         CH$_3$ | CH$_2$CH$_2$OH | O—isomer | 139–145° |
| 32 | HO—CH$_2$CH$_2$CH$_2$Cl | NaH | DDMF | —(CH$_2$)$_2$— | CH$_2$CH$_2$CH$_2$OH | O—isomer | 108° |

[(1)]DMF = Dimethylformamide
[(2)]DME = Dimethoxyethane

The compounds which follows (examples 33 to 35) are obtained from example 29 and 30, O-isomer and N-isomer, respectively, according to the following procedure: 0.03 mole of the starting compound are heated to the boiling temperature in 10% hydrochloric acid (100 ml) for about 2 hours.

Then the solvent is evaporated off, the residue is oven-dried under vacuum and crystallized from methanol.

EXAMPLE 33

2-[(6,7,8,9-Tetrahydro-1,3-dimethyl-3H-pyrazolo[3,4-c][2,7]naphthiridin-5-yl]-oxy-ethanol, hydrochloride M.p. 252°–255° C.

EXAMPLE 34

6,7,8,9-Tetrahydro-1,3-dimethyl-5-methoxy-3H-pyrazolo[3,4-c][2,7]naphthiridine, hydrochloride M.p. 276°–277° C.

EXAMPLE 35

6,7,8,9-Tetrahydro-1,3,4-trimethyl-3H-pyrazolo[3,4-c][2,7]naphthiridin-5-(4H)-one, hydrochloride M.p. 290°–293° C.

EXAMPLE 36

7-Acetyl-4-(2-chloroethyl)-6,7,8,9-tetrahydro-1,3-dimethyl-3H-pyrazolo[3,4-c][2,7]naphthiridin-5-(4H)-one 7-Acetyl-5-(2-hydroxyethoxy)-6,7,8,9-tetrahydro-1,3-dimethyl-3H-pyrazolo[3,4-c][2,7]naphthiridin-5-(4H)-one (0.0328 mole) is dissolved in chloroform (200 ml) and 5.95 g (0.05 mole) of thionyl chloride in methylene chloride (30 ml) are added thereto; the resulting mixture is heated to the reflux temperature for about 3 hours. After cooling, 400 ml of aqueous saturated sodium carbonate is added to the reaction mixture, the organic phase is separated and the organic solvent is evaporated under reduced pressure. The obtained solid is crystallized from ethyl alcohol, yielding the product of the title. M.p. 195°–198° C.

EXAMPLE 37

5-(3-Chloropropoxy)-6,7,8,9-tetrahydro-1,3-dimethyl-3H-pyrazolo[3,4-c]isoquinoline Obtained substantially by following the above procedure, but starting from the compound of example 32. M.p. 84°–85° C.

EXAMPLE 38

7-Acetyl-4-[2-(diethylamino)ethyl]-6,7,8,9-tetrahydro-1,3-dimethyl-3H-pyrazolo[3,4-c][2,7]naphthiridin-5-(4H)-one, hydrochloride 0.031 Mole of the compound of example 36; 12.79 ml (0.0124 mole) of diethylamine, and 300 ml of ethanol are heated at about 80° C. for about 3 hours. After evaporating the solvent under vacuum the reaction mass is taken up with chloroform, and the organic layer is first washed with saturated aqueous sodium carbonate and then with water (twice). After drying over sodium sulfate, the chloroform is distilled off and the obtained concentrate is applied to a silica gel column prepared and eluted with chloroform/methanol, 97:3. The product of the title is obtained by evaporating the solvent from the pooled fractions containing it. M.p. 153°–154° C.

By essentially following the above procedure, employing the reagents, solvents and conditions indicated in Table III, the following compound of formula

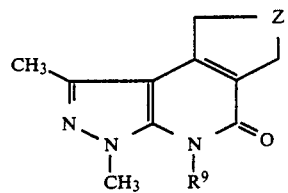

wherein $R^9$ and Z have the meaning set forth in the table, are obtained starting from the corresponding compounds wherein $R^9$ is the suitable halo($C_{2-3}$)alkyl.

TABLE III

| Example No. | Reagent | Solvent | Temp./time (°C./h) | Z | $R^9$ | M.p. °C. |
|---|---|---|---|---|---|---|
| 39 | HN(C₂H₅)₂ | toluene | reflux/7 h | CH₂ | —(CH₂)₂—N(C₂H₅)₂ | 186–188°(+) |
| 40 | HN⌒N—Ph | toluene and triethylamine | reflux 14 h | —CH₂— | —(CH₂)₂—N⌒N—Ph | 155–157° |
| 41 | HN(CH₃)₂ | toluene | 60°/16 h | —(CH₂)₂— | —(CH₂)₂N(CH₃)₂ | 113–115° |
| 42 | HN(C₂H₅)₂ | benzene | reflux/8 h | —(CH₂)₂— | —(CH₂)₂N(C₂H₅)₂ | 184–187°(+) |
| 43 | HN⌒ | toluene and triethylamine | reflux/14 h | —(CH₂)₂— | —(CH₂)₂—N⌒ | 90–93° |
| 44 | H₂N—(n-C₄H₉) | toluene | 60°/6 h | —(CH₂)₂ | —(CH₂)NH—(n-C₄H₉) | 100–102° |
| 45 | HN⌒N—CH₃ | toluene | reflux/6 h | —(CH₂)₂ | —(CH₂)₂—N⌒N—CH₃ | 231–234° |

TABLE III-continued

| Example No. | Reagent | Solvent | Temp./time (°C./h) | Z | R⁹ | M.p. °C. |
|---|---|---|---|---|---|---|
| 46 | HN⟨⟩N—Ph | toluene and triethylamine | reflux/7 h | —(CH₂)₂— | —(CH₂)—N⟨⟩N—PH | 195–198° (oxalate). |
| 47 | HN(CH₃)₂ | ethanol and triethylamine | 60°/3 h | —CH₂—N(COCH₃)— | —(CH₂)₂—N(CH₃)₂ | 96–99° |
| 48 | HN⟨⟩N—Ph | ethanol and triethylamine | reflux/3 h | —CH₂—N(COCH₃)— | —(CH₂)₂—N⟨⟩N—Ph | 187–189° |

(⁻)Characterized in the form of the corresponding oxalates

The compounds of the following examples (table IV) are obtained by reacting 10 g of the corresponding N-acetyl derivative of formula XII (the compounds of examples 47, and 48, respectively) with saturated hydrochloric acid at room temperature for about 1 hour. The organic phase is then concentrated under vacuum and dried. The dichloridrates of examples 49 and 50 crystallizes from ethanol or methanol. The compound of 51 (free base) crystallizes from ethyl acetate.

TABLE IV

| Example No. | X | R⁹ | M.p. (°C.) |
|---|---|---|---|
| 49 | —CH₂—NH— | —(CH₂)₂—N(CH₃)₂ | 289–291°(+) |
| 50 | —CH₂NH— | —(CH₂)₂—N(C₂H₅)₂ | 274–275°(+) |
| 51 | —CH₂NH— | —(CH₂)—N⟨⟩N—Ph | 154–159° |

(+)Hydrochloride

EXAMPLE 52

N-[1,3-dimethyl-4-(4-methyl-1-cyclohexen-1-yl)-1H-pyrazol-5-yl]formamide

To a suspension of 1,3-dimethyl-4-(4-methyl-1-cyclohexen-1-yl)-5-(1H)-pyrazolamine (24.5 g; 0.119 mole) in 99% formic acid (245 ml), acetic acid anhydride (64.14 g, 0.628 mole) is added at a temperature of about 20° C. Then the mixture is heated to 80°–90° C. and kept at this temperature for about 2 hours. After distillation of the solvent under vacuum, the residue is taken up with water and the pH is adjusted to about 8 with aqueous sodium carbonate. The solution is extracted with methylene chloride and the organic layer is washed with water and then dried over sodium sulfate. After distillation of the solvent, the crude product of the title is recovered and crystallized from the mixture t.butylmethyl-ether and hexane. M.p. 97°–99° C.

EXAMPLE 53

6,7,8,9-Tetrahydro-1,3,7-trimethyl-3H-pyrazolo[3,4-c]isoquinoline

Phosphorusoxychloride, POCl₃ (61.33 g) is added to the compound of the above example 52 (N-[1,3-dimethyl-4-(4-methyl-1-cyclohexen-1-yl)-1H-pyrazolo-5-yl]formamide) (27.8 g) in xylene (250 ml). The mixture is refluxed for 4 hours and then distilled under vacuum. The residue is taken up with water and the pH is adjusted to about 8 with aqueous sodium carbonate. Upon filtering, 17 g of the crude product of the title are obtained. M.p. 92°–101° C., after crystallization from petroleum ether.

EXAMPLE 54

6,7,8,9-Tetrahydro-1,3,8-trimethyl-3H-pyrazolo[3,4-c]isoquinoline (a) Acetic acid anhydride (64.14 g; 0.628 mol) is added to 1,3-dimethyl-4-(5-methyl-1-cyclohexen-1-yl)-5-pyrazolamine (24.5 g; 0.119 mol) in 99% formic acid (245 ml) under stirring at about 20° C. The mixture is slowly heated to 80°–90° C. and then kept at this temperature for about 2 hours. The solvent and the reagent excess are then distilled off under reduced pressure, while the residue is taken up with water and adjusted to about pH 8 with aqueous sodium carbonate. The resulting solution is extracted with methylene chloride and the organic layer is washed with water and dried over sodium sulfate. The solvent is evaporated under vacuum thus recovering the N-[1,3-dimethyl-4-(5-methyl-1H-cyclohexen-1-yl)-1H-pyrazol-5-yl]formamide derivative.

(b) the crude derivative obtained above is dissolved in xylene (250 ml) and POCl₃ (61.33 g) is added thereto. The mixture is refluxed for 4 hours and then the solvent is distilled under reduced pressure. The residue is poured into water and the pH is adjusted to about 8 with aqueous sodium bicarbonate. A precipitate forms, the product of the title, which is recovered by filtration and crystallized from hexane. M.p. 121°–123° C.

Essentially following the procedure of the above example, the compounds of formula I listed in table V below are obtained.

TABLE V

| Example No. | R | R¹ | R² | R³ | R⁸ | M.p. (°C.) |
|---|---|---|---|---|---|---|
| 55 | CH₃ | CH₃ | —(CH₂)₃— | | H | 245–247°(*) |

4,612,318

TABLE V-continued

| Example No. | R | R¹ | R² | R³ | R⁸ | M.p. (°C.) |
|---|---|---|---|---|---|---|
| 56 | CH₃ | CH₃ | —(CH₂)₃— | | CH₃ | 132–133° |
| 57 | CH₃ | CH₃ | —(CH₂)₄— | | H | 108–110° |
| 58 | CH₃ | CH₃ | —(CH₂)₄— | | CH₃ | 116–117° |
| 59 | CH₃ | CH₃ | —(CH₃)₄— | | —CH₂—C₆H₅ 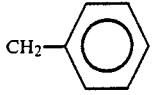 | 128–129° |
| 60 | CH₃ | CH₃ | —(CH₂)₄— | | —CH₂—C₆H₃(OCH₃)₂ 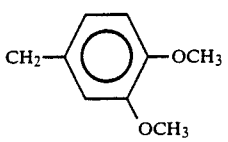 | 113–114° |
| 61 | CH₃ | CH₃ | —(CH₂)₅— | | H | 203–206°(*) |
| 62 | CH₃ | CH₃ | C₆H₅  | CH₃ | H | 93–95° |
| 63 | CH₃ | CH₃ | C₆H₅  | CH₃ | CH₃ | 98–102° |
| 64 | CH₃ | CH₃ | C₆H₅  | CH₃ | —CH₂—C₆H₅ 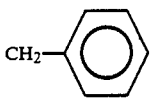 | 136–137° |
| 65 | CH₃ | C₂H₅ | —(CH₂)₄— | | H | |
| 66 | CH₃ | i-C₃H₇ | —(CH₂)₄— | | H | |
| 67 | CH₃ | n-C₃H₇ | —(CH₂)₃— | | H | |
| 68 | CH₃ | t-C₄H₉ | —(CH₂)₄— | | H | |
| 69 | CH₃ | i-C₄H₉ | —(CH₂)₄— | | H | |
| 70 | CH₃ | n-C₄H₉ | —(CH₂)₄— | | H | |
| 71 | CH₃ | cyclopropyl  | —(CH₂)₅— | | H | |
| 72 | CH₃ | cyclopentyl  | —(CH₂)₄— | | H | |
| 73 | CH₃ | cyclohexyl 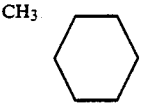 | —(CH₂)₄— | | H | |
| 74 | CH₃ | t-C₄H₉ | —CH₂—NH—CH₂CH₂—   (CH₃) | | H | |
| 75 | CH₃ | i-C₄H₉ | —CH₂—CH₂—N—CH₂—   (CH₃) | | H | |
| 76 | CH₃ | n-C₄H₉ | —CH₂—CH₂—N—CH₂—   (COCH₃) | | H | |
| 77 | CH₃ | cyclopropyl  | —CH₂—N—CH₂—   (COCH₃) | | H | |

TABLE V-continued

| Example No. | R | R¹ | R² | R³ | R⁸ | M.p. (°C.) |
|---|---|---|---|---|---|---|
| 78 | $CH_3$ | cyclopentyl | $-CH_2-N(CH_3)-CH_2-$ | | H | |
| 79 | $CH_3$ | cyclohexyl | $-CH_2-N(CH_3)-CH_2CH_2-$ | | H | |
| 80 | $CH_3$ | t-$C_4H_9$ | $-CH_2-CH_2-N(CH_3)-CH_2-$ | | H | |
| 81 | $CH_3$ | i-$C_4H_9$ | $-CH_2-CH_2-N(COCH_3)-CH_2-$ | | H | |
| 82 | $CH_3$ | n-$C_4H_9$ | $-CH_2-N(COCH_3)-CH_2-$ | | H | |
| 83 | $CH_3$ | cyclopropyl | $-CH_2-N(CH_3)-CH_2-$ | | H | |
| 84 | $CH_3$ | cyclopentyl | $-CH_2-NH-CH_2CH_2-$ (with $CH_3$) | | H | |
| 85 | $CH_3$ | cyclohexyl | $-CH_2-CH_2-N(CH_3)-CH_2-$ | | H | |

(*)obtained in the form of the corresponding hydrochlorides

EXAMPLE 86

A tablet is prepared with

| | |
|---|---|
| 6,7,8,9-tetrahydro-1,3-dimethyl-3H—pyrazolo[3,4-c]isoquinoline, hydrochloride | 150 mg |
| Saccharose | 30 mg |
| Polyvinylpyrrolidone | 5 mg |
| Sodium dioctylsulfosuccinate | 1.4 mg |
| Magnesium stearate | 8 mg |
| Corn starch | q.s. to 250 mg |

EXAMPLE 87

A capsule is prepared with

| | |
|---|---|
| 6,7,8,9-tetrahydro-1,3-dimethyl-3H—pyrazolo[3,4-c]isoquinoline, hydrochloride | 200 mg |
| Saccharose | 35 mg |
| Polyvinylpyrrolidone | 5 mg |
| Sodium dioctylsulfosuccinate | 1.8 mg |
| Magnesium stearate | 10 mg |
| Corn starch | q.s. to 300 mg |

EXAMPLE 88

A sugar coated tablet is prepared with

| | |
|---|---|
| 6,7,8,9-tetrahydro-1,3-dimethyl-3H—pyrazolo[3,4-c]isoquinoline, hydrochloride | 50 mg |
| Polyvinylpyrrolidone | 2 mg |
| Sodium carboxymethylcellulose | 1.5 mg |
| Avicel ® | 5 mg |
| Titanium dioxide | 2 mg |
| Magnesium stearate | 2.5 mg |
| Corn starch | 8 mg |
| Gum arabic | 5 mg |
| Talc | 10 mg |
| Kaolin | 2 mg |
| Saccharose | q.s. to 150 mg |

Avicel ® is a Trademark of FMC Co., U.S.A.

I claim:

1. A pyrazolo[3,4-b]pyridine having the formula

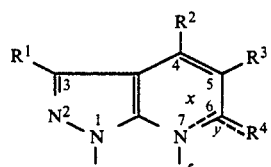

or a physiologically acceptable acid addition salt thereof wherein

R and R¹ independently represent ($C_{1-6}$)alkyl, ($C_{3-7}$)cycloalkyl, phenyl, substituted phenyl, phenyl($C_{1-4}$)alkyl, or substituted phenyl($C_{1-4}$)alkyl;

R² and R³ taken together represent a $-(CH_2)_n-$ group wherein n is an integer selected from 3, 4 and 5, and where one of the —CH$_2$—groups may be substituted with the group

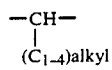

R$^4$ represents R$^8$ or —OR$^9$;
R$^8$ represents hydrogen, (C$_{1-4}$)alkyl, phenyl, substituted phenyl, phenyl(C$_{1-4}$)alkyl, substituted pheny(C$_{1-4}$)alkyl;
R$^9$ represents hydrogen, (C$_{1-4}$)alkyl, (C$_{2-6}$)alkanoyl-(C$_{1-4}$)alkyl, hydroxy(C$_{2-4}$)alkyl, halo(C$_{2-4}$)alkyl, amino(C$_{2-4}$)alkyl, or mono- or di-(C$_{1-4}$)alkylamino((C$_{2-4}$)alkyl;
R$^5$ represents nil, x is an additional bond, and y is nil with the proviso that when R$^4$ is R$^8$, R$^2$ must be different from methyl, wherein the term "substituted phenyl" alone or in combination with other groups, refers to a phenyl group wherein one, two or three hydrogen atoms are replaced by substituents independently selected from, chloro, bromo, fluoro, cyano, nitro, hydroxy, mercapto, trifluoromethyl, (C$_{1-4}$)alkyl, (C$_{2-4}$)alkenyl, (C$_{3-7}$)cycloalkyl, (C$_{1-4}$)alkoxy, (C$_{1-4}$)alkylthio, (C$_{1-4}$)alkoxycarbonyl, carboxy(C$_{1-4}$)alkyl, carboxy(C$_{3-7}$)cycloalkyl, sulfynyl, and (C$_{1-4}$)alkylsulfynyl.

2. A compound as in claim 1 wherein
R is (C$_{1-6}$)alkyl or (C$_{3-7}$)cycloalkyl,
R$^1$ represents (C$_{1-4}$)alkyl,
R$^2$ and R$^3$ taken together represent —(CH$_2$)$_n$—group wherein n is an integer selected from 3 or 4, and wherein one of the —(CH$_2$)$_n$—groups is substituted with

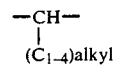

or a pharmaceutically acceptable acid addition salt thereof.

3. A compound which is 6,7,8,9-tetrahydro-1,3-dimethyl-3H-pyrazolo[3,4-c]isoquinoline or a pharmaceutically acceptable acid addition salt thereof.

4. A CNS-depressant or analgesic composition comprising a CNS-depressant or analgetic effective amount of a compound according to claim 1, in combination with a pharmaceutically acceptable carrier or diluent.

* * * * *

UNITED STATES PATENT AND TRADEMARK OFFICE
CERTIFICATE OF CORRECTION

PATENT NO. : 4,612,318

DATED : September 16, 1986

INVENTOR(S) : Giorgio Winters

It is certified that error appears in the above-identified patent and that said Letters Patent are hereby corrected as shown below:

On the face page, Column 1 at Foreign Application Priority Data the serial number reads "22375 A/82" and should read --23375 A/82 --.

At column 1, line 13, the patent reads "pyrazolo pyridine" and should read --pyrazolo[3,4-b]pyridine--.

At column 2, lines 40 and 41, the patent reads "carboxy($C_{1-4}$)alkyl, carboxy-($C_{3-7}$)cycloalkyl," and should read --carbo($C_{1-4}$)alkyl, carbo($C_{3-7}$)cycloalkyl,--.

At column 4, line 26, the patent reads "thiazolo and pyrazolo isoquinoline" and should read --thiazolo[5,4-c] and pyrazolo[3,4-c]isoquinoline--.

At column 7, line 12, the patent reads "a substrate of" and should read --a substrate of formula I--.

At columns 15 and 16, line 45, Example 26, the patent reads "$CH_3J$" and should read --$CH_3I$--.

At columns 15 and 16, line 48, Example 29, under the column heading m.p.(b.p.), the patent reads "196-172°" and should read --196-201°--.

At columns 15 and 16, Example 29, under the column heading Reagent, the patent reads "$CH_3J$" and should read --$CH_3I$--.

At columns 15 and 16, Examples 29/30, under the column heading Basic Compound, the patent reads "$\begin{pmatrix} NaH_{mx,1} \\ K_2CO_3 \\ K_2CO_3 \end{pmatrix}$" and should read --$\begin{pmatrix} NaH \\ K_2CO_3 \\ K_2CO_3 \end{pmatrix}$--.

UNITED STATES PATENT AND TRADEMARK OFFICE
CERTIFICATE OF CORRECTION

PATENT NO. : 4,612,318

DATED : September 16, 1986

INVENTOR(S) : Giorgio Winters

It is certified that error appears in the above-identified patent and that said Letters Patent are hereby corrected as shown below:

At columns 15 and 16, Example 32, under the column heading Solvent, the patent reads "DDMF" and should read --DMF--.

At columns 17 and 18, Table III, Example 45, under the column heading m.p.°C, the patent reads "231-234°" and should read --231-234°(+)--.

At column 19, line 22, the patent preads "examples 47, and 48, respectively" and should read --examples 47, 38 and 48, respectively--.

Signed and Sealed this

Twenty-ninth Day of March, 1988

Attest:

DONALD J. QUIGG

*Attesting Officer*  *Commissioner of Patents and Trademarks*